United States Patent
Womack et al.

(10) Patent No.: US 10,638,779 B2
(45) Date of Patent: May 5, 2020

(54) HEMIACETYL PROFLAVORS

(71) Applicant: FIRMENICH SA, Satigny (CH)

(72) Inventors: Gary B. Womack, Plainsboro, NJ (US); Matthew Sillick, Belle Mead, NJ (US)

(73) Assignee: Firmenich SA, Satigny (CH)

( * ) Notice: Subject to any disclaimer, the term of this patent is extended or adjusted under 35 U.S.C. 154(b) by 150 days.

(21) Appl. No.: 15/538,506

(22) PCT Filed: Dec. 21, 2015

(86) PCT No.: PCT/EP2015/080717
§ 371 (c)(1),
(2) Date: Jun. 21, 2017

(87) PCT Pub. No.: WO2016/102424
PCT Pub. Date: Jun. 30, 2016

(65) Prior Publication Data
US 2017/0339986 A1 Nov. 30, 2017

Related U.S. Application Data

(60) Provisional application No. 62/096,830, filed on Dec. 24, 2014.

(51) Int. Cl.
| | | |
|---|---|---|
| *A23L 27/29* | (2016.01) | |
| *A23L 2/56* | (2006.01) | |
| *C07D 307/12* | (2006.01) | |
| *C07C 69/38* | (2006.01) | |
| *C07C 69/40* | (2006.01) | |
| *C07C 69/44* | (2006.01) | |
| *C07C 69/60* | (2006.01) | |
| *A23L 27/20* | (2016.01) | |

(52) U.S. Cl.
CPC ............. *A23L 2/56* (2013.01); *A23L 27/2028* (2016.08); *A23L 27/29* (2016.08); *C07C 69/38* (2013.01); *C07C 69/40* (2013.01); *C07C 69/44* (2013.01); *C07C 69/60* (2013.01); *A23V 2002/00* (2013.01)

(58) Field of Classification Search
CPC ...... A23L 27/79; A23L 27/2028; A23L 27/29; A23L 2/56; A23L 27/2024; C07D 307/12; C07C 69/38; C07C 69/40; C07C 69/44; C07C 69/60
See application file for complete search history.

(56) References Cited

U.S. PATENT DOCUMENTS

| | | | |
|---|---|---|---|
| 5,079,023 A | 1/1992 | DeSimone | |
| 2015/0232691 A1* | 8/2015 | Webster | C08F 222/02 523/400 |
| 2017/0044089 A1* | 2/2017 | Messana | C08F 2/44 |

FOREIGN PATENT DOCUMENTS

| | | |
|---|---|---|
| JP | 2000159843 A | 6/2000 |
| JP | 2003252883 A | 9/2003 |
| JP | 2004119307 A | 4/2004 |
| JP | 2013156563 A | 8/2013 |
| JP | 2013182040 A | 9/2013 |
| WO | WO2002028345 A2 | 4/2002 |
| WO | WO2014043720 A1 | 3/2014 |

OTHER PUBLICATIONS

International Search Report and Written Opinion, application PCT/EP2015/080717 dated Mar. 22, 2016.
Yamamoto et al, "New thermosetting coatings using blocked carboxyl groups," Progress in Organic Coatings, vol. 40, No. 1-4, 2000, pp. 267-273.

* cited by examiner

*Primary Examiner* — Nikki H. Dees
*Assistant Examiner* — Changqing Li
(74) *Attorney, Agent, or Firm* — Armstrong Teasdale LLP

(57) ABSTRACT

Provided herein is a compound having the formula I

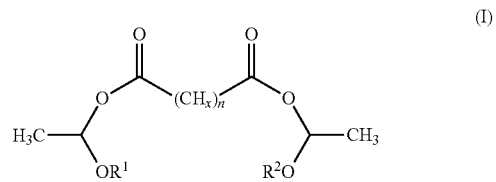

wherein $R^1$ and $R^2$ are independently selected from a branched or straight $C_{1-6}$ alkyl and a $C_{1-6}$ alkenyl, n is 1, 2, 3, 4, 5, or 6 and x is independently 0, 1, or 2; provided that when n is 1, x is 2. Also provided herein is a method of releasing acetaldehyde into an aqueous solution including delivering a compound of formula I to the aqueous solution. Also provided is a flavor or aroma-modifying composition including i) a flavor or aroma-conferring or modifying ingredient, at least one compound according to formula (I); ii) at least one ingredient selected from the group consisting of a flavor carrier and a flavor base; and iii) optionally at least one flavor adjuvant.

9 Claims, No Drawings

HEMIACETYL PROFLAVORS

RELATED APPLICATIONS

This application is a national stage application under 35 U.S.C. § 371 filing of International Patent Application PCT/EP2015/080717, filed Dec. 21. 2015, which claims the benefit of U.S. Provisional Application 62/096,830, filed Dec. 24, 2014.

FIELD

Provided herein are precursors to acetaldehyde and their use for delivering acetaldehyde to food and beverages to typically provide increase flavor.

BACKGROUND

Acetaldehyde is an important, yet difficult to encapsulate flavor ingredient. It is used in a large variety of flavors but is particularly appreciated in fruit flavors where it imparts important aspects of freshness and juiciness to the flavors. The volatility of acetaldehyde also provides lift to the aroma greatly contributing to the olfactive impact of the flavor. Thus the use of acetaldehyde is indispensable for creating flavors where these effects are desired such as in beverages. However, with a boiling point of 20-21° C., it is a difficult material to use due to evaporation during handling which in turn can create unsafe situations due to overexposure to personnel and the risk of fire. Once incorporated into a liquid flavor, loss of acetaldehyde due to evaporation is still a concern which also can make handling such flavors difficult. In addition to being highly volatile, acetaldehyde is a very reactive chemical. It can react with alcohols in flavor formulations to form acetals; it can engage in aldol condensation reactions; it is susceptible to oxidation; and it can trimerize to form paraldehyde. In addition to losing acetaldehyde by these chemical reactions, the products formed can change the character of the flavor and in the worst case contribute unwanted off-flavors.

SUMMARY

Provided herein is a compound having the formula I:

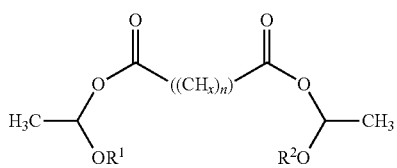

wherein R1 and R2 are independently selected from a branched or straight $C_1$-$C_6$ alkyl and a $C_1$-$C_6$ alkenyl, n is 1, 2, 3, 4, 5 or 6 and x is independently 0, 1 or 2; provided that when n is 1, x is 2.

Also provided herein is a method of releasing acetaldehyde into an aqueous solution comprising delivering a compound of formula I

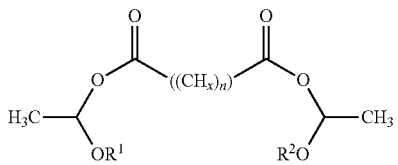

to the aqueous solution wherein R1 and R2 are independently selected from a branched or straight $C_1$-$C_6$ alkyl and a $C_1$-$C_6$ alkenyl, n is 1, 2, 3, 4, 5 or 6 and x is independently 0, 1 or 2; provided that when n is 1, x is 2.

Also provided herein is a use of a compound of formula I

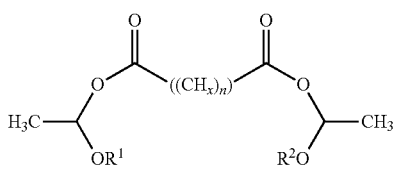

as an ingredient to confer, enhance, improve or modify the flavor or aroma of a flavored article wherein R1 and R2 are independently selected from a branched or straight $C_1$-$C_6$ alkyl and a $C_1$-$C_6$ alkenyl, n is independently 1, 2, 3, 4, 5 or 6 and x is independently 0, 1 or 2; provided that when n is 1, x is 2.

Still yet further provided herein is a flavor or aroma-modifying composition comprising:
i) a flavor or aroma-conferring or modifying ingredient, at least one compound according to formula (I) above;
ii) at least one ingredient selected from the group consisting of a flavor carrier and a flavor base; and
iii) optionally at least one flavor adjuvant.

DETAILED DESCRIPTION

For the Summary, Description and Claims, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of".

Further provided herein is a compound of formula I wherein $R^1$ and $R^2$ are independently a straight or branched $C_1$-$C_4$ akyl.

In one embodiment, provided herein is a compound of formula I wherein $R^1$ and $R^2$ are independently selected from the group consisting of methyl, ethyl, propyl, and butyl.

In another embodiment, provided herein is a compound of formula I wherein n is 1 and x is 2.

In another embodiment, provided herein is a compound of formula I wherein n is 2 and x is independently 0, 1 or 2.

In another embodiment, provided herein is a compound of formula I wherein n is 3, 4, 5 or 6 and x is independently 0, 1 or 2.

In another embodiment, provided herein is a compound of formula I selected from the group consisting of: bis(1-ethoxyethyl) succinate; bis(1-ethoxyethyl) adipate; bis(1-ethoxyethyl) fumarate; bis(1-propoxyethyl) succinate; bis(1-propoxyethyl) adipate; bis(1-propoxyethyl) fumarate; bis(1-butoxyethyl) succinate; bis(1-butoxyethyl) adipate, and bis(1-butoxyethyl) fumarate.

In particular, provided herein is a compound of formula I selected from the group consisting of bis(1-ethoxyethyl) succinate; bis(1-ethoxyethyl) adipate; bis(1-ethoxyethyl) fumarate; bis(1-propoxyethyl) succinate; bis(1-propoxyethyl) adipate; bis(1-propoxyethyl) fumarate; bis(1-butoxyethyl) succinate; and bis(1-butoxyethyl) adipate.

In another embodiment, provided herein is a compound of formula I comprising bis(1-ethoxyethyl) succinate.

In another embodiment, provided herein is a compound of formula I comprising bis(1-propoxyethyl) succinate.

In another embodiment, provided herein is a compound of formula I comprising bis(1-butoxyethyl) succinate.

In another embodiment, provided herein is a compound of formula I comprising bis(1-ethoxyethyl) adipate.

In another embodiment, provided herein is a compound of formula I comprising bis(1-propoxyethyl) adipate.

In another embodiment, provided herein is a compound of formula I comprising bis(1-butoxyethyl) adipate.

In another embodiment, provided herein is a compound of formula I comprising bis(1-ethoxyethyl) fumarate.

In another embodiment, provided herein is a compound of formula I comprising bis(1-propoxyethyl) fumarate.

In another embodiment, provided herein is a compound of formula I comprising bis(1-butoxyethyl) fumarate.

In one embodiment, provided herein is a compound of formula I provided that the compound is not bis(1-ethoxyethyl) adipate.

By "flavor carrier" we mean here a material which is substantially neutral from a flavor point of view, insofar as it does not significantly alter the organoleptic properties of flavoring ingredients. The carrier may be a liquid or a solid.

Suitable liquid carriers include, for instance, an emulsifying system, i.e. a solvent and a surfactant system, or a solvent commonly used in flavors. A detailed description of the nature and type of solvents commonly used in flavor cannot be exhaustive. Suitable solvents include, for instance, propylene glycol, triacetin, triethyl citrate, benzylic alcohol, ethanol, vegetable oils or terpenes.

Suitable solid carriers include, for instance, absorbing gums or polymers, or even encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's Verlag-GmbH & Co., Hamburg, 1996. Encapsulation is a well-known process to a person skilled in the art, and may be performed, for instance, using techniques such as spray-drying, agglomeration, extrusion, coacervation and the like.

In one embodiment, the compounds provided herein are provided in a "flavor base" i.e., a composition comprising at least one additional flavoring ingredient. In one embodiment, said additional flavoring ingredient is not a compound of formula (I). Moreover, by "flavoring ingredient" it is meant here a compound, which is used in flavoring preparations or compositions to impart a hedonic effect. In other words such an ingredient, to be considered as being a flavoring one, must be recognized by a person skilled in the art as being able to impart or modify in a positive or pleasant way the flavor or aroma of a composition, and not just as having a flavor or aroma.

The nature and type of the flavoring co-ingredients present in the base do not warrant a more detailed description here, the skilled person being able to select them on the basis of his/her general knowledge and according to intended use or application and the desired organoleptic effect. In general terms, these flavoring co-ingredients belong to chemical classes as varied as alcohols, aldehydes, ketones, esters, ethers, acetates, nitriles, terpenoids, nitrogenous or sulphurous heterocyclic compounds and essential oils, and said flavoring co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of flavor. It is also understood that said co-ingredients may also be compounds known to release in a controlled manner various types of flavoring compounds.

By "flavor carrier" we mean here a material which is substantially neutral from a flavor point of view, insofar as it does not significantly alter the organoleptic properties of flavoring ingredients. The carrier may be a liquid or a solid.

Suitable liquid carriers include, for instance, an emulsifying system, i.e. a solvent and a surfactant system, or a solvent commonly used in flavors. A detailed description of the nature and type of solvents commonly used in flavor cannot be exhaustive. Suitable solvents include, for instance, propylene glycol, triacetin, triethyl citrate, benzylic alcohol, ethanol, vegetable oils or terpenes.

Suitable solid carriers include, for instance, absorbing gums or polymers, or even encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's Verlag-GmbH & Co., Hamburg, 1996. Encapsulation is a well-known process to a person skilled in the art, and may be performed, for instance, using techniques such as spray-drying, agglomeration, extrusion, coacervation and the like.

A composition consisting of at least one compound of formula (I) and at least one flavor carrier represents a particular embodiment of the invention as well as a flavoring composition comprising at least one compound of formula (I), at least one flavor carrier, at least one flavor base, and optionally at least one flavor adjuvant.

Moreover, a compound of formula (I) can be advantageously incorporated into flavored articles to positively impart, or modify, the flavor, freshness, the fruitiness, the juiciness or aroma of said articles. Thus, in yet another aspect, the present invention provides a flavored article comprising:

i) a compound of formula (I), as defined above; and
ii) a foodstuff base.

For the sake of clarity, it has to be mentioned that, by "foodstuff" we mean here an edible product, e.g. a food or a beverage. Therefore, a flavored article according to the invention comprises one or more compounds according to formula (I), as well as optional benefit agents, corresponding to flavor or aroma and flavor or aroma profile of the desired edible product. The compositions and methods provided herein have use in food or beverage products. When the food product is a particulate or powdery food, the dry particles may easily be added thereto by dry-mixing. Typical food products are selected from the group consisting of an instant soup or sauce, a breakfast cereal, a powdered milk, a baby food, a powdered drink, a powdered chocolate drink, a spread, a powdered cereal drink, a chewing gum, an effervescent tablet, a cereal bar, and a chocolate bar. The powdered foods or drinks may be intended to be consumed after reconstitution of the product with water, milk and/or a juice, or another aqueous liquid.

Suitable foodstuff bases, e.g. foods or beverages, include dairy and confectionery products where a fresh or fruity tonality is desired.

In another embodiment provided herein is a fluid dairy product including, without limitation to, non-frozen, partially frozen and frozen fluid dairy products such as, for example, milks, ice creams, sorbets and yogurts.

In one embodiment, the compositions and compounds provided herein provide "fresh", "juicy" and "fruity" flavor and/or aroma to a food article.

Beverage products include, without limitation, carbonated soft drinks, including cola, lemon-lime, root beer, heavy citrus ("dew type"), fruit flavored and cream sodas; powdered soft drinks, as well as liquid concentrates such as fountain syrups and cordials; coffee and coffee-based drinks, coffee substitutes and cereal-based beverages; teas, including dry mix products as well as ready-to-drink teas (herbal and tealeaf based); fruit and vegetable juices and juice flavored beverages as well as juice drinks, nectars, concentrates, punches and "ades"; sweetened and flavored waters, both carbonated and still; sport/energy/health drinks; alcoholic beverages plus alcohol-free and other low-alcohol products including beer and malt beverages, cider, and wines (still, sparkling, fortified wines and wine coolers); other beverages processed with heating (infusions, pasteurization, ultra high temperature, ohmic heating or commercial aseptic sterilization) and hot-filled packaging; and cold-filled products made through filtration or other preservation techniques. The nature and type of the constituents of the foodstuffs or beverages do not warrant a more detailed description here, the skilled person being able to select them on the basis of his general knowledge and according to the nature of said product.

In the case of flavoring compositions, typical concentrations of the compounds provided herein are in the range of, by weight, of about 0.01% to 15%, particularly from about 1% to about 15%, more particularly from about 1% to about 5%, and more particularly from about 1% to about 2% of the total weight of the compositions. In one embodiment, the concentration of the compounds provided herein in a flavored article are in the range, by weight, of about 3 ppm to about 60 ppm, particularly from about 3 ppm to about 30 ppm, more particularly from about 10 ppm to about 30 ppm, even more particularly from about 10 ppm to 20 ppm based on the total weight of the flavored article.

In another embodiment, the compounds provided herein are provided in an amount in a flavored article such that the compounds provide, by weight, acetaldehyde in an amount that ranges from about 1 ppm to about 20 ppm, more particularly from about 1 ppm to about 10 ppm, more particularly from 4 ppm to about 10 ppm, even more particularly from about 4 ppm to about 6 ppm of the total weight of the article.

By "flavor base" we mean here a composition comprising at least one flavoring ingredient.

Said flavoring ingredient is not a compound of formula (I). Moreover, by "flavoring ingredient" it is meant here a compound, which is used in flavoring preparations or compositions to impart a hedonic effect. In other words such an ingredient, to be considered as being a flavoring one, must be recognized by a person skilled in the art as being able to impart or modify in a positive or pleasant way the flavor of a composition, and not just as having a flavor.

The nature and type of the flavoring co-ingredients present in the base do not warrant a more detailed description here, the skilled person being able to select them on the basis of his general knowledge and according to intended use or application and the desired organoleptic effect. In general terms, these flavoring co-ingredients belong to chemical classes as varied as alcohols, aldehydes, ketones, esters, ethers, acetates, nitriles, terpenoids, nitrogenous or sulphurous heterocyclic compounds and essential oils, and said flavoring, co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of flavor. It is also understood that said co-ingredients may also be compounds known to release in a controlled manner various types of flavoring compounds.

By "flavor adjuvant" we mean here an ingredient capable of imparting additional added benefit such as a color, a particular light resistance, chemical stability, and so on. A detailed description of the nature and type of adjuvant commonly used in flavoring bases cannot be exhaustive. Nevertheless, such adjuvants are well-known to a person skilled in the art, but it has to be mentioned that said ingredients are well-known to a person skilled in the art.

For the sake of clarity, it has to be mentioned that, by "foodstuff" we mean here an edible product, e.g. a food or a beverage. Therefore, a flavored article according to the invention comprises one or more compounds according to formula (I), as well as optional benefit agents, corresponding to a flavor or aroma profile of the desired edible product, e.g. a savory cube.

Further provided herein is a spray-dried particle comprising a compound of formula I.

Further provided herein is a preparation of a spray dried particle comprising: a) preparing a spray dried feed emulsion comprising an emulsifier, maltodextrin, and a compound of Formula I wherein the emulsion has a buffer that regulates the pH between 6 and 9. The emulsifiers can be selected from the group consisting of gum Arabic, saponin, and modified starch. The emulsion may also contain optional ingredients. It may in particular further contain an effective amount of a fireproofing or explosion suppression agents. The type and concentration of such agents in spray-drying emulsions is known to the person skilled in the art. One can cite as non-limiting examples of such fireproofing or explosion suppression agents inorganic salts, $C_1$-$C_{12}$ carboxylic acids, salts of $C_1$-$C_{12}$ carboxylic acids and mixtures thereof. Particular explosion suppression agents are, salicylic acid, acetic acid, propionic acid, butyric acid, isobutyric acid, valeric acid, caproic acid, citric acid, succinic acid, hydroxysuccinic acid, maleic acid, fumaric acid, oxylic acid, glyoxylic acid, adipic acid, lactic acid, tartaric acid, ascorbic acid, the potassium, calcium and/or sodium slats of any of the afore-mentioned acids, and mixtures of any of these. Other optional ingredients include antioxidants, colorants and dyes.

The emulsion can be formed using any known emulsifying method, such as high shear mixing, sonication or homogenization. Such emulsifying methods are well known to the person skilled in the art.

The droplet size d(v,0.9) of the emulsion is particularly comprised between 1 and 15 μm, more particularly between 1 and 10 μm and even more particularly between 1 and 20 μm. More particularly, the droplet size remains within the range for at least one day storage at ambient temperature (25° C.).

The viscosity of the emulsion is particularly between 20 and 300 mPas, more particularly between 70 and 200 mPas and even more particularly between 100 and 150 mPas at the temperature at which the atomization step, as defined below, is conducted.

After the emulsion is prepared, it is then spray-dried so as to obtain dry particles. The spray-drying process comprises two steps, the first one being dispersion and the second one being drying. The emulsion is first subjected to an atomization step, during which the emulsion is dispersed in the form of drops into a spraying tower. Any device capable of dispersing the emulsion in the form of drops can be used to carry out such dispersion. For instance, the emulsion can be guided through a spraying nozzle or through a centrifugal wheel disk into the spraying tower. Vibrated orifices may also be used. The size of the capsules is determined by the size of the drops that are dispersed into the tower. If a spraying nozzle is used for dispersing the drops the size may be controlled by the flow rate of an atomizing gas through the nozzle, for example. In the case where a centrifugal wheel disk is used for dispersal, the main factor for adjusting droplet size is the centrifugal force with which the drops are dispersed from the disk into the tower. The centrifugal force, in turn, depends on the speed of rotation and the diameter of the disk. The feed flow rate of the emulsion, its surface tension and its viscosity are also parameters controlling the final drop size and size distribution. By adjusting these parameters, the skilled person can control the size of the drops of the emulsion to be dispersed in the tower.

Once sprayed in the chamber, the droplets are dried using any technique known in the art. These methods are perfectly documented in the patent and non-patent literature in the art of spray-drying. For example, Spray-Drying Handbook, 3rd ed., K. Masters; John Wiley (1979), describes a wide variety of spray-drying methods.

A process provided herein may be performed in any conventional spraying tower. A conventional multi-stage drying apparatus is for example appropriate for conducting the steps of this process. It may comprise a spraying tower, and, at the bottom of the tower, a fluidised bed intercepting partially dried particles after falling through the tower.

The following Examples are provided for illustrative purposes only and are not meant to be limiting in any manner.

EXAMPLES

Preparation of Hemiacetal Esters Set Forth in Examples 1-9 was Carried as Essentially Described Below:

In a typical procedure, a mixture of the dicarboxylic acid (70-100 mmol), p-toluenesulfonic acid (0.1 mol %) and diethyl ether (50 mL) was cooled in an ice bath. The alkyl vinyl ether (3 equiv) dissolved in diethyl ether (50 mL) was added dropwise over 15-30 min. The mixture was removed from the cold bath and stirred at room temperature for 4-20 h. Five grams of sodium carbonate was added and the mixture concentrated with a rotary evaporator. The product was isolated by bulb-to-bulb distillation to afford the hemiacetal esters as colorless oils.

Example 1

Bis(1-ethoxyethyl) succinate

The title compound was prepared in 93% yield from 85 mmol of succinic acid and 255 mmol of ethyl vinyl ether.

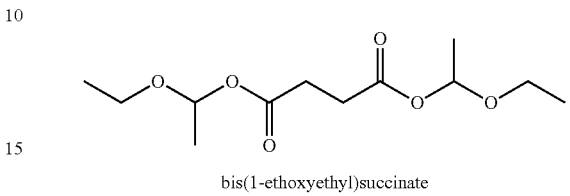

bis(1-ethoxyethyl)succinate $^1$H NMR (CDCl$_3$, 400 MHz): δ 1.21 (t, J=7.1 Hz, 6H), 1.40 (d, J=5.2 Hz, 6H), 2.57-2.73 (m, 4H), 3.53 (dq, J=7.1, 9.5 Hz, 2H), 3.72 (dq, J=7.1, 9.5 Hz, 2H), 5.96 (q, J=5.2 Hz, 2H).

MS (EI): 262 (M$^+$, 0), 145 (4), 101 (11), 89 (6), 73 (100), 45 (32).

Example 2

Bis(1-ethoxyethyl) adipate

The title compound was prepared in 92% yield from 68.7 mmol of adipic acid and 207 mmol of ethyl vinyl ether.

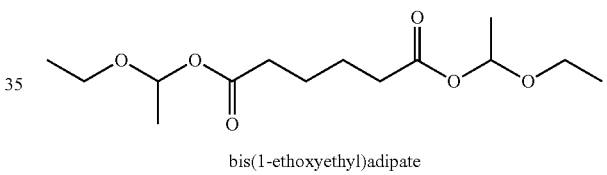

bis(1-ethoxyethyl)adipate $^1$H NMR (CDCl$_3$, 400 MHz): δ 1.21 (t, J=7.1 Hz, 6H), 1.39 (d, J=5.2 Hz, 6H), 1.65-1.72 (m, 4H), 2.32-2.39 (m, 4H), 3.53 (dq, J=7.1, 9.5 Hz, 2H), 3.70 (dq, J=7.1, 9.5 Hz, 2H), 5.94 (q, J=5.2 Hz, 2H).

MS (EI): 290 (M$^+$, 0), 201 (1), 173 (1), 129 (6), 101 (1), 73 (100), 55 (5), 45 (33).

Example 3

Bis(1-propoxyethyl) succinate

The title compound was prepared in 28% yield (based on the vinyl ether) from 246 mmol of succinic acid and 246 mmol of propyl vinyl ether.

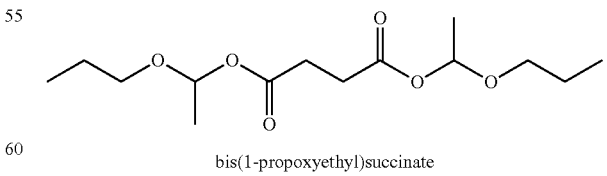

bis(1-propoxyethyl)succinate $^1$H NMR (CDCl$_3$, 400 MHz): δ 0.92 (t, J=7.4 Hz, 6H), 1.40 (d, J=5.3 Hz, 6H), 1.59 (sextet, J=7.2 Hz, 4H), 2.59-2.71 (m, 4H), 3.42 (overlapping dt, J=6.7, 9.3 Hz, 2H), 3.62 (overlapping dt, J=6.7, 9.3 Hz, 2H), 5.94 (overlapping q, J=5.3 Hz, 2H).

MS (EI): 290 (M+, 0), 159 (2), 103 (3), 101 (7), 87 (100), 56 (3), 45 (33), 43 (18), 41 (6).

Example 4

Bis(1-propoxyethyl) adipate

The title compound was prepared in 87% yield from 70.1 mmol of adipic acid and 211 mmol of propyl vinyl ether.

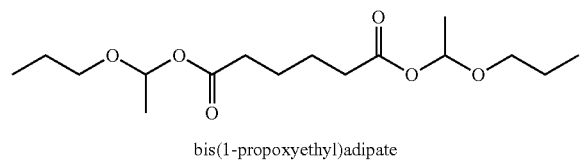 [SMILES: CCCOC(C)OC(=O)CCCCC(=O)OC(C)OCCC]

bis(1-propoxyethyl)adipate $^1$H NMR (CDCl$_3$, 400 MHz): δ 0.92 (t, J=7.4 Hz, 6H), 1.39 (d, J=5.3 Hz, 6H), 1.59 (sextet, J=7.2 Hz, 4H), 1.66-1.72 (m, 4H), 2.31-2.40 (m, 4H), 3.43 (dt, J=6.8, 9.5 Hz, 2H), 3.60 (dt, J=6.8, 9.5 Hz, 2H), 5.93 (q, J=5.3 Hz, 2H).

MS (EI): 318 (M+, 0), 215 (1), 129 (17), 111 (8), 100 (28), 87 (100), 86 (25), 69 (8), 55 (17), 45 (51), 44 (38), 43 (59), 42 (15).

Example 5

Bis(1-propoxyethyl) fumarate

The title compound was prepared in 39% yield from 89 mmol of fumaric acid and 277 mmol of propyl vinyl ether.

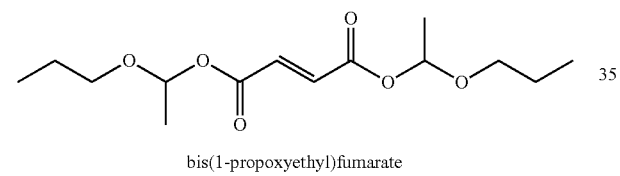

bis(1-propoxyethyl)fumarate $^1$H NMR (CDCl$_3$, 400 MHz): δ 0.93 (t, J=7.4 Hz, 6H), 1.46 (d, J=5.3 Hz, 6H), 1.60 (sextet, J=6.8 Hz, 4H), 3.46 (dt, J=9.4, 6.8 Hz, 2H), 3.64 (dt, J=9.4, 6.8 Hz, 2H), 6.03 (q, J=5.3 Hz, 2H), 6.87 (s, 2H).

MS (EI): 288 (M+, 0), 229 (<1), 185 (2), 143 (3), 125 (5), 99 (16), 87 (71), 86 (41), 71 (13), 45 (59), 44 (80), 43 (100), 42 (21), 41 (64).

Example 6

Bis(1-butoxyethyl) succinate

The title compound was prepared in 64% yield from 86 mmol of succinic acid and 259 mmol of butyl vinyl ether.

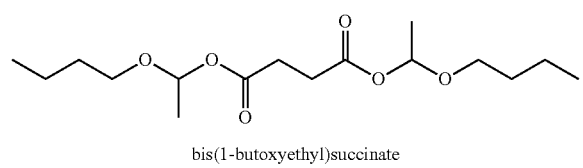 [SMILES: CCCCOC(C)OC(=O)CCC(=O)OC(C)OCCCC]

bis(1-butoxyethyl)succinate $^1$H NMR (CDCl$_3$, 400 MHz): δ 0.92 (t, J=7.4 Hz, 6H), 1.37 (sextet, J=7.5 Hz, 4H), 1.39 (d, J=5.3 Hz, 6H), 1.55 (quintet, J=7.1 Hz, 4H), 2.59-2.70 (m, 4H), 3.43-3.50 (m, 2H), 3.63-3.69 (m, 2H), 5.94 (overlapping quartets, J=5.3 Hz, 2H).

MS (EI): 274 (M+, 0), 173 (1), 117 (4), 101 (80), 100 (28), 85 (51), 57 (85), 56 (100), 45 (37), 44 (31), 43 (21), 42 (11), 41 (93).

Example 7

Bis(1-butoxyethyl) adipate

The title compound was prepared in 50% yield (based on the vinyl ether) from 206 mmol of adipic acid and 206 mmol of butyl vinyl ether.

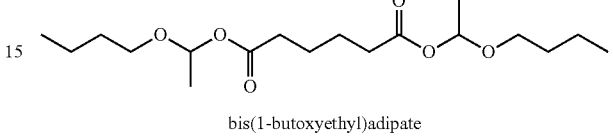

bis(1-butoxyethyl)adipate $^1$H NMR (CDCl$_3$, 400 MHz): δ 0.91 (t, J=7.4 Hz, 6H), 1.37 (sextet, J=7.4 Hz, 4H), 1.39 (d, J=5.3 Hz, 6H), 1.55 (quintet, J=7.1 Hz, 4H), 1.65-1.73 (m, 4H), 2.30-2.40 (m, 4H), 3.47 (dt, J=6.7, 9.5 Hz, 2H), 3.64 (dt, J=6.7, 9.5 Hz, 2H), 5.92 (q, J=5.3 Hz, 2H).

MS (EI): 346 (M+, 0), 201 (1), 129 (17), 111 (7), 101 (100), 100 (78), 85 (57), 73 (10), 69 (12), 60 (13), 57 (86), 56 (90), 55 (38), 45 (48), 41 (95).

Example 8

Bis(1-ethoxyethyl) fumarate

The title compound was prepared in 59% yield from 86 mmol of fumaric acid and 277 mmol of ethyl vinyl ether.

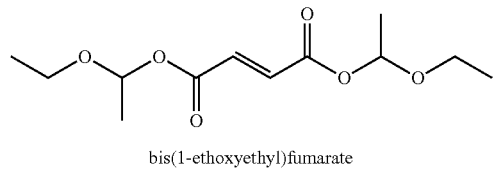 [SMILES: CCOC(C)OC(=O)/C=C/C(=O)OC(C)OCC]

bis(1-ethoxyethyl)fumarate $^1$H NMR (CDCl$_3$, 400 MHz): δ 1.22 (t, J=7.1 Hz, 6H), 1.46 (d, J=5.4 Hz, 6H), 3.57 (dq, J=7.1, 9.5 Hz), 3.74 (dq, J=7.1, 9.5 Hz), 6.04 (q, J=5.4 Hz, 2H), 6.87 (s, 2 Hz).

MS (EI): 260 (M+, 0), 215 (<1), 171 (3), 143 (2), 125 (4), 99 (20), 73 (100), 72 (35), 45 (46), 44 (40), 43 (45).

Example 9

Bis(1-ethoxyethyl) malonate

The title compound was prepared in 72% yield from 96 mmol of malonic acid and 349 mmol of ethyl vinyl ether.

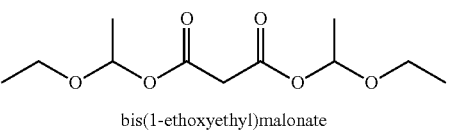 [SMILES: CCOC(C)OC(=O)CC(=O)OC(C)OCC]

bis(1-ethoxyethyl)malonate $^1$H NMR (CDCl$_3$, 400 MHz): δ 1.214 and 1.216 (both t, J=7.1 Hz, 6H), 1.427 and 1.429 (both d, J=5.3 Hz, 6H), 3.41 (overlapping d, J=2.9 Hz, 2H), 3.53-3.60 (m, 2H), 3.75-3.81 (m, 2H), 5.989 and 5.992 (both q, J=5.3 Hz, 2H).

MS (EI): (M+, 0), 175 (<1), 131 (<1), 117 (<1), 89 (3), 87 (5), 73 (100), 68 (3), 60 (4), 45 (75), 43 (31).

Example 10

Synthesis of Comparative Sample: 1-ethoxyethyl acetate

Diethyl ether (50 mL), glacial acetic acid (10 g, 167 mmol) and p-toluenesulfonic acid (0.01 g) were combined and the mixture was cooled in an ice bath. Ethyl vinyl ether (18 g, 250 mmol) in 50 mL of diethyl ether was added dropwise over 15 minutes. The mixture was removed from the cold bath and stirred for two hours at room temperature. Sodium carbonate (5 g) was added and the mixture was filtered. Diethyl ether was removed by fractional distillation at atmospheric pressure. Fractional distillation of the residue yielded 17.7 g (34-35° C., 19 mbar) of 1-ethoxyethyl acetate (134 mmol, 80% yield).

$^1$H NMR (CDCl$_3$, 400 MHz): δ 1.21 (t, J=7.1 Hz, 3H), 1.40 (d, J=5.2 Hz, 3H), 2.07 (s, 3H), 3.49-3.77 (m, 2H), 5.93 (q, J=5.2 Hz, 1H).

MS (EI): 132 (M+, 0), 131 (<1), 117 (3), 89 (5), 87 (12), 73 (55), 45 (61), 43 (100).

Example 11

Assessment of Hydrolysis Rate at pH 3.0

Instant beverage applications require rapid hydrolysis of the precursor molecules in order to rapidly release acetaldehyde. Because such beverages might be consumed immediately upon preparation, it is desired for the release to be as rapid as possible.

A pH 3.0 buffer solution was prepared by adding 16.43 g citric acid (CAS 77-92-9) and 4.26 g disodium citrate (CAS 144-33-2) to 1 L of deionized water. Aliquots of the Examples 1, 2 and 10 preparations were added to the buffer solution within a Distek 2100B USP 2 dissolution system stirring at 200 rpm. The concentration of acetaldehyde in solution was monitored as a function of time using a UV/Vis spectrometer probe which measured absorbance at 276 nm every 1 second. Release followed first order kinetics and half lives are reported in Table 1. Results for comparative samples were taken from work by Gassenmeier et al. [1]. A sample of acetaldehyde diethyl acetal was also measured directly and the result was similar to that reported by Gassenmeier et al. Examples 1, 2 and 10 released acetaldehyde faster than Comparative Samples 2-5.

TABLE 1

Half life of acetaldehyde precursors at pH 3

| Compound | Half life (s) at pH 3.0 |
|---|---|
| Example 1: bis(1-ethoxyethyl) succinate | 96 |
| Example 2: bis(1-ethoxyethyl) adipate | 185 |
| Example 10: Comparative Sample 1: 1-ethoxyethyl acetate | 31 |
| Comparative Sample 2: Acetaldehyde diethyl acetal (measured for this work) | 539 |
| Comparative Sample 3: Acetaldehyde diethyl acetal [1] | 579 |
| Comparative Sample 4: 1-ethoxy-1-(1-ethoxy-ethoxy)-ethane [1] | 306 |
| Comparative Sample 5: 1,2-di[(1'-ethoxy) ethoxy] propane; Aldemax ® [1] | 625 |

[1] Gassenmeier, K., Daniher, A., Furrer, S., 1-Ethoxy-1-(1-ethoxy-ethoxy)-ethane: a new acetaldehyde precursor, in: Wender, L. P. B. (Ed.), Developments in Food Science Flavour Science Recent Advances and Trends, Elsevier, 2006, pp. 305-308.

Example 12

Assessment of Hydrolysis Rate Under Spray Driving Feed Conditions

Acetaldehyde precursors suitable for rendering into dry powders must avoid releasing significant levels of acetaldehyde during various stages of processing. In particular they should resist hydrolysis during the preparation of a spray drying feed emulsion, which can be neutral to basic pH and can contain a significant volume fraction of an oil phase.

A pH 8.0 buffer solution was prepared by adding 49.92 g disodium phosphate heptahydrate (CAS 7782-85-6) and 1.93 g monosodium phosphate (CAS 7558-80-7) to 1 L of deionised water. Aliquots of 0.20 g of the Examples 1, 2 and 10 preparations were dissolved in 0.8 g of limonene (CAS 5989-25-7) added to 10 g of the buffer solution within a 30 mL Erlenmeyer flask containing a stir bar. The concentration of acetaldehyde in solution was monitored as a function of time using a UV/Vis spectrometer probe measuring absorbance at 276 nm. Stirring was periodically stopped to allow oil droplets to rise to the surface and collect an unobscured absorbance reading of the aqueous solution. Release followed mixed zero and first order kinetics. $t_{50}$ (the time to 50% of the maximum absorbance) values are reported in Table 2. Comparative Sample 1 has $t_{50}$ of 2.1 minutes, which is so short that a person skilled in the art would consider this compound at risk of experiencing a problematic degree of hydrolysis during processing. Surprisingly, despite similarity of the functional groups, Examples 1 and 2 have longer $t_{50}$ values and released acetaldehyde more slowly than Comparative Sample 1.

TABLE 2

$t_{50}$ of acetaldehyde precursors at pH 8 in emulsions

| Compound | $t_{50}$ at pH 8.0 |
|---|---|
| Example 1: bis(1-ethoxyethyl) succinate | 14.0 min |
| Example 2: bis(1-ethoxyethyl) adipate | 44.6 min |
| Example 10: Comparative Sample 1: 1-ethoxyethyl acetate | 2.1 min |

Example 13

Preparation of Spray Dried Powders

Spray-drying feed emulsions were prepared according to Table 3. The amount of each precursor molecule was chosen to produce 0.25 g acetaldehyde based on stoichiometry. The Example 1-2 liquids were dissolved into the orange flavor. This mixture was added to the salt, maltodextrin, water and saponin solution and mixed for 2 minutes using a homogenizer (T25 UlraTurrax, IKA Works, USA). The preparation was then spray dried (model 190 Mini-Spray Drier, Buchi Corporation, New Castle Del., USA) with inlet air temperature set to 138° C. and outlet air temperature of 95° C.

TABLE 3

Spray drying feed formula

| Compound | Spray Dry A | Spray Dry B | Spray Dry C |
|---|---|---|---|
| Example 1: bis(1-ethoxyethyl) succinate | 0.77 g | — | — |
| Example 2: bis(1-ethoxyethyl) adipate | — | 0.82 g | — |

TABLE 3-continued

Spray drying feed formula

| Compound | Spray Dry A | Spray Dry B | Spray Dry C |
|---|---|---|---|
| Nat Orange WONF (596407 A) 567407A, Firmenich Inc, Plainsboro, NJ, USA) | 8.40 g | 8.40 g | 8.40 g |
| Maltodextrin (Glucidex IT 19, Roquette Corporation, Lestrem, France) | 40.5 g | 40.5 g | 40.5 g |
| Deionised water | 40.5 g | 40.5 g | 40.5 g |
| Monosodium phosphate (CAS 7558-80-7) | 0.05 g | 0.05 g | 0.05 g |
| Disodium phosphate heptahydrate (CAS 7782-85-6) | 0.50 g | 0.50 g | 0.50 g |
| Saponin solution (Q-Naturale 200, Ingedion Incorporated, West Chester, IL, USA) | 1.00 g | 1.00 g | 1.00 g |

Example 14

Preparation and Evaluation of Instant Beverages

Spray Dry preparations A, B and C were reconstituted by combining 0.1 g of the preparation with 0.07 g citric acid, 7 g sucrose and dissolving the mixture in 100 mL of distilled water.

The beverages were prepared quickly and tasted by a panel of 5 individuals. All five found the beverages prepared from Spray Dry A and B to be fresher and riper than the beverage prepared from Spray Dry C.

1) Analysis of Acetaldehyde Yield

The concentration of acetaldehyde derived from Spray Dry A-C was measured using reverse phase HPLC after dissolving the powder in water and derivatizing with 2,4-dinitrophenylhydrazine. Results in Table 4 show that high levels of acetaldehyde are liberated from Spray Dry powders A and B.

Acetaldehyde Concentration in Spray Dried Powders

| Powder | Acetaldehyde concentration (g/100 g) |
|---|---|
| Spray Dry A: bis(1-ethoxyethyl) succinate | 0.49 |
| Spray Dry B: bis(1-ethoxyethyl) adipate | 0.53 |
| Spray Dry C: control - orange oil | 0.05 |

The invention claimed is:

1. A method of releasing an acetaldehyde into an aqueous solution, the method comprising delivering an acetaldehyde precursor compound of formula (I):

$$\text{H}_3\text{C}-\underset{\text{OR}^1}{\overset{}{\text{CH}}}-\text{O}-\underset{\text{O}}{\overset{\text{O}}{\text{C}}}-((\text{CH}_x)_n)-\underset{\text{O}}{\overset{\text{O}}{\text{C}}}-\text{O}-\underset{\text{R}^2\text{O}}{\overset{}{\text{CH}}}-\text{CH}_3 \quad (I)$$

to the aqueous solution wherein $R^1$ and $R^2$ are independently selected from a branched or straight $C_1$-$C_6$ alkyl and a $C_1$-$C_6$ alkenyl, n is 1, 2, 3, 4, 5 or 6, and x is independently 0, 1 or 2, provided that when n is 1, x is 2, wherein the acetaldehyde is a flavor ingredient, a flavor-modifying ingredient, an aroma-conferring ingredient, or an aroma-modifying ingredient, and wherein the acetaldehyde is released by hydrolysis of the acetaldehyde precursor compound of formula (I).

2. The method as recited in claim 1 wherein $R^1$ and $R^2$ are independently a straight or branched $C_1$-$C_4$ alkyl.

3. The method as recited in claim 2 wherein $R^1$ and $R^2$ are independently selected from the group consisting of methyl, ethyl, propyl, and butyl.

4. The method as recited in claim 1 wherein n is 1 and x is 2.

5. The method as recited in claim 1 wherein n is 2 and x is independently 0, 1 or 2.

6. The method as recited in 1 wherein the compound of formula I is selected from the group consisting of bis(1-ethoxyethyl) succinate; bis(1-ethoxyethyl) adipate; bis(1-ethoxyethyl) fumarate; bis(1-propoxyethyl) succinate; bis (1-propoxyethyl) adipate; bis(1-propoxyethyl) fumarate; bis (1-butoxyethyl) succinate; bis(1-butoxyethyl) adipate, and bis(1-butoxyethyl) fumarate.

7. A flavor-modifying composition comprising:
i) at least one acetaldehyde precursor compound according to formula (I)

$$\text{H}_3\text{C}-\underset{\text{OR}^1}{\overset{}{\text{CH}}}-\text{O}-\underset{\text{O}}{\overset{\text{O}}{\text{C}}}-((\text{CH}_x)_n)-\underset{\text{O}}{\overset{\text{O}}{\text{C}}}-\text{O}-\underset{\text{R}^2\text{O}}{\overset{}{\text{CH}}}-\text{CH}_3 \quad (I)$$

wherein $R^1$ and $R^2$ are independently selected from a branched or straight $C_1$-$C_6$ alkyl and a $C_1$-$C_6$ alkenyl, n is 1, 2, 3, 4, 5 or 6, and x is independently 0, 1 or 2, provided that when n is 1, x is 2, wherein the acetaldehyde precursor compound of formula (I) is capable of hydrolysis in an aqueous solution to release an acetaldehyde into the aqueous solution, and wherein the acetaldehyde is a flavor ingredient, a flavor-modifying ingredient, an aroma-conferring ingredient, or an aroma-modifying ingredient;

ii) at least one ingredient selected from the group consisting of a flavor carrier and a flavor base; and iii) optionally at least one flavor adjuvant.

8. A flavored article comprising:
i) at least one acetaldehyde precursor compound of formula (I)

$$\text{H}_3\text{C}-\underset{\text{OR}^1}{\overset{}{\text{CH}}}-\text{O}-\underset{\text{O}}{\overset{\text{O}}{\text{C}}}-((\text{CH}_x)_n)-\underset{\text{O}}{\overset{\text{O}}{\text{C}}}-\text{O}-\underset{\text{R}^2\text{O}}{\overset{}{\text{CH}}}-\text{CH}_3 \quad (I)$$

wherein $R^1$ and $R^2$ are independently selected from a branched or straight $C_1$-$C_6$ alkyl and a $C_1$-$C_6$ alkenyl, n is 1, 2, 3, 4, 5 or 6, and x is independently 0, 1 or 2, provided that when n is 1, x is 2, wherein the acetaldehyde precursor compound of formula (I) is capable of hydrolysis in an aqueous solution to release an acetaldehyde into the aqueous solution, and wherein the acetaldehyde is a flavor ingredient, a flavor-modifying ingredient, an aroma-conferring ingredient, or an aroma-modifying ingredient; and ii) a foodstuff base.

9. A flavored article comprising:
i) the flavor-modifying composition of claim 7; and
ii) a foodstuff base.

\* \* \* \* \*

UNITED STATES PATENT AND TRADEMARK OFFICE
CERTIFICATE OF CORRECTION

| | |
|---|---|
| PATENT NO. | : 10,638,779 B2 |
| APPLICATION NO. | : 15/538506 |
| DATED | : May 5, 2020 |
| INVENTOR(S) | : Womack et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 241 days.

Signed and Sealed this
Thirty-first Day of January, 2023

Katherine Kelly Vidal
*Director of the United States Patent and Trademark Office*